United States Patent [19]

Metz et al.

[11] Patent Number: 5,346,482
[45] Date of Patent: Sep. 13, 1994

[54] TWO-PIECE OSTOMY APPLIANCE HAVING FLUSHABLE POUCH AND FACEPLATE WITH PROTECTIVE COLLAR

[75] Inventors: Michael Metz, Chicago; James J. Peterson, Island Lake, both of Ill.

[73] Assignee: Hollister Incorporated, Libertyville, Ill.

[21] Appl. No.: 42,008

[22] Filed: Apr. 2, 1993

[51] Int. Cl.$^5$ .............................................. A61F 5/44
[52] U.S. Cl. .................................. 604/338; 604/332; 604/339; 604/342
[58] Field of Search ........................... 604/332–345

[56] References Cited

U.S. PATENT DOCUMENTS

| | | | |
|---|---|---|---|
| 4,419,100 | 12/1983 | Alexander | 604/339 |
| 4,460,363 | 7/1984 | Steer et al. | 604/339 |
| 4,610,676 | 9/1986 | Schneider et al. | 604/339 |
| 4,610,677 | 9/1986 | Mohiuddin | 604/339 |
| 4,772,279 | 9/1988 | Brooks et al. | 604/339 |
| 4,917,689 | 4/1990 | Coombes | 604/338 |
| 5,009,648 | 4/1991 | Aronoff et al. | 604/338 |
| 5,160,330 | 11/1992 | Cross | 604/338 |

FOREIGN PATENT DOCUMENTS 2083762 2/1985 United Kingdom .

*Primary Examiner*—Randall L. Green
*Assistant Examiner*—Rob Clarke
*Attorney, Agent, or Firm*—Tilton, Fallon, Lungmus

[57] ABSTRACT

A two-piece ostomy appliance is disclosed having a faceplate component and a pouch component, the faceplate component including a flexible attachment ring having an annular outer flange portion and an inner collar portion for insertion into the side opening of the pouch component when the two are releasably joined together. The flushable pouch has a pair of side walls joined together along their outer margins with each wall comprising a primary layer of strong but water-soluble material and a protective inner layer of relatively weak but water-insoluble material. When the components are adhesively joined together, the protective collar of the faceplate attachment ring extends into the side opening of the pouch to shield the edge (or edges) of the water-soluble layer (or layers) from exposure to fluids and other matter discharged through the stoma-receiving opening of the faceplate into the pouch, thereby protecting the water-soluble layer(s) from premature disintegration.

10 Claims, 1 Drawing Sheet

TWO-PIECE OSTOMY APPLIANCE HAVING FLUSHABLE POUCH AND FACEPLATE WITH PROTECTIVE COLLAR

BACKGROUND AND SUMMARY

This invention relates to a two-piece ostomy appliance having a faceplate component and a pouch component wherein the faceplate has a protective collar for shielding surrounding edges of the water-soluble layer (or layers) of the pouch from fluids which pass through the side opening in the pouch wall.

Two-piece ostomy appliances having faceplate components and pouch components are well known in the art. For examples of such devices, reference may be had to co-owned U.S. Pat. Nos. 4,419,100, 4,610,676 and 4,610,677.

Recently it has been considered desirable to provide flushable ostomy pouches that may be discarded into toilet bowls or water closets. The walls or panels of such a pouch are typically composed of at least two layers, specifically, a tough flexible, but water-soluble or water-dispersible primary layer which gives the pouch its structural integrity and a thin, water-insoluble inner layer which lines the inside of the pouch and prevents the pouch's contents from contacting and dissolving the primary layer when the pouch is worn. Although the primary layer gives the pouch its strength, once the pouch is discarded into the bowl of a flush toilet, the primary layer, being exposed to water in the bowl, quickly dissolves allowing the weaker interior layer to disintegrate and disperse by the turbulence of water when the toilet is flushed.

A characteristic shortcoming of such a system is that either an edge of the primary water-soluble layer is left exposed about the stoma-receiving side opening of the pouch where it may be contacted by aqueous body fluids discharged into the pouch that could result in premature disintegration of the pouch while it is being worn, or some additional means or manufacturing technique must be utilized to protect such edge from contact with effluent. The first of these approaches assumes that the risk of pouch failure may be minimized by limiting the length of time a given pouch is worn (see U.S. Pat. No. 4,772,279), whereas the second approach necessarily increases the complexity and cost of pouch construction and manufacture and may also have the undesirable result of weakening the structure of the pouch in the region of its stoma-receiving opening. Examples of this second approach are found in U.S. Pat. Nos. 4,917,689 (an additional ring or flange is secured to the inner layer and extends through the stoma-receiving opening of the pouch to cover the edge of the dissolvable primary layer), 4,772,279 (the background portion of this patent discloses an inner layer that projects beyond the edge of the primary layer and is sealed to an annular outer member to conceal the edge of the primary layer), and UK patent 2,083,762B (a gum ring is applied to the pouch to cover the annular edge of the primary layer). In these specific examples, the techniques involve modifying the construction of the pouches themselves to avoid or reduce the risk of exposing the edge of primary layers to contact with fluids passing though the stoma-receiving openings. Such expedients, in addition to the disadvantages of complexity and expense already mentioned, may also have the undesirable effect of reducing the flushability of the pouches by adding protective elements that may be substantially insoluble in the water of a toilet bowl or sewage system.

The present invention addresses the above problems by providing a two-piece appliance in which the means for protecting the annular edge of the primary layer is provided not by the pouch itself but by the faceplate component. Specifically, the separate faceplate component is equipped with an attachment ring having a protective annular collar which is inserted into the stoma-receiving opening (or side opening) of the pouch component when the parts are joined together. By providing the faceplate component with means for shielding the exposed edge of the water-soluble or dispersible primary layer of the pouch component, as well as the edge of any other water-soluble element provided by the pouch about its stoma-receiving opening, the pouch component may be easily and relatively inexpensively manufactured, since the pouch component does not require its own protective flange or gum ring permanently affixed about its stoma-receiving opening and does not necessitate special manufacturing steps such as the removal or concealment of an edge portion of the pouch's primary or exterior layer during manufacture. In a preferred embodiment, the pouch component of the present invention is provided with a thin, flexible, adhesive-coated mounting ring, ideally formed of water-soluble polymeric material, exteriorly affixed to the pouch about its stoma-receiving opening. After removal of a release sheet that covers the adhesive coating of the mounting ring, the axially-extending collar of the faceplate attachment ring is inserted into the opening of the pouch. The collar therefore serves as a locating element to guide proper assembly of the parts in addition to performing its primary function of shielding the edges of the water-soluble layer(s) of the pouch when the components are sealed together.

Other features, advantages, and objects of the invention will become apparent from the specification and drawings.

DRAWINGS

DETAILED DESCRIPTION OF PREFERRED EMBODIMENT

Figure 1:
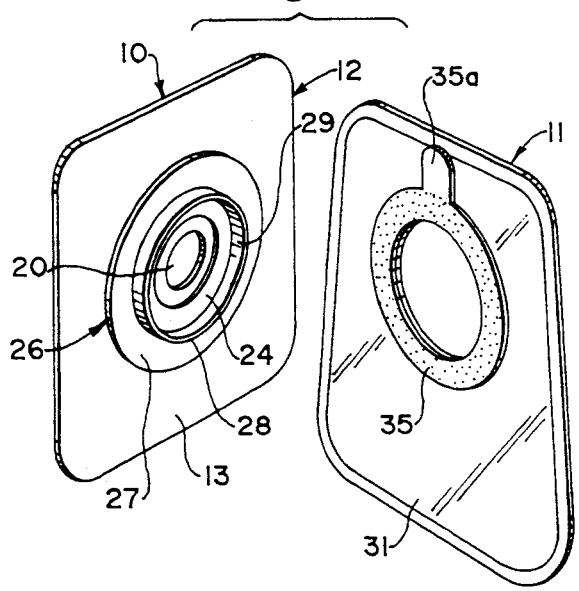
FIG. 1 is a perspective view of a two-piece ostomy appliance embodying this invention, the appliance being shown with the pouch component and faceplate component uncoupled.
Figure 2:
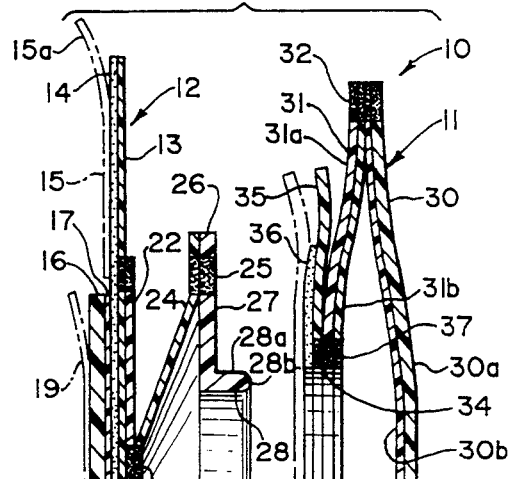
FIG. 2 is an enlarged, somewhat schematic cross-sectional view showing the features of the faceplate component and the pouch component in separated condition.

In FIGS. 1 and 2, the numeral 10 generally designates a two-piece ostomy appliance comprising a pouch component 11 and a faceplate component 12. The faceplate component 12 comprises a thin, flexible patch or panel 13 preferably formed of microporous sheet material or other suitable sheet material provided with a coating of pressure-sensitive adhesive 14 along one surface for peristomal attachment to a patient. A removable release sheet 15 of siliconized paper (shown only in phantom) covers the adhesive coating 14 until use, such sheet preferably having a pull tab 15a to facilitate such removal. If desired, the faceplate may also be provided on its patient-facing side with a layer 16 of soft, pliant skin barrier material which has both wet and dry tack and forms an effective moisture seal against a patent's skin. Example of suitable hydrocolloid skin barrier materials are well known in the art as disclosed in co-owned U.S. Pat. Nos. 4,477,325 and 4,496,357. Preferably, the barrier layer 16 is provided with a thin, flexible thermoplastic film 17 on its pouch-facing side which is heat sealed to the microporous patch or panel 13 (FIG. 2). Like the surface of adhesive layer 14, the exposed surface or patient-facing surface of barrier layer 16 may be covered by a suitable release sheet 19 to be removed at the time of application. The faceplate 12 has a stoma-receiving opening 20 which may be reformed or enlarged by cutting prior to application so as to conform generally with the size and shape of the patient's stoma.

In the embodiment illustrated, the microporous patch 13 is heat sealed at 21 to a thin, flexible, thermoplastic annular web 22 which in turn is heat sealed at 23 to a second annular web 24. Along its outer periphery, web 24 is heat sealed (at 25) to the outer edge portion of an relatively stiff but nevertheless flexible, molded thermoplastic attachment ring 26. It is to be understood that, if desired, the webs 22, 23 may be omitted and the attaching ring 26 may be secured directly to patch 13. However, in the preferred embodiment shown, the attachment ring 26 is allowed to "float" so that a user may grasp the back of ring 26 and avoid applying pressure against the sensitive peristomal area of the patient's body when the components are being coupled together. For a more detailed description of such a floating construction and its advantages, reference may be had to co-owned U.S. Pat. No. 4,419,100.

Figure 3:
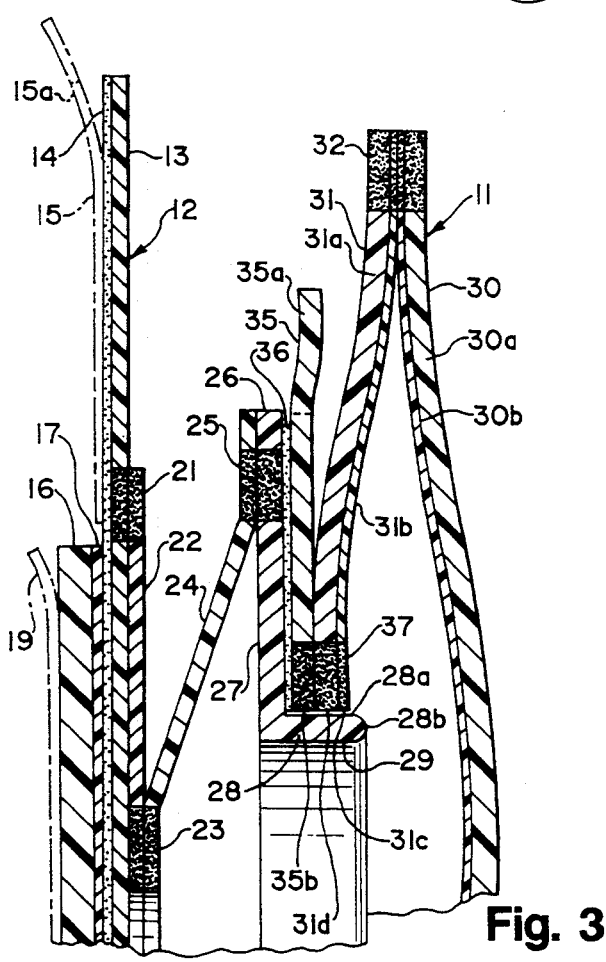
FIG. 3 is a still further enlarged, fragmentary cross-sectional view with the faceplate component and the pouch component in coupled condition.

Attachment ring 26 may be molded of any tough, durable, substantially water-insoluble thermoplastic material that has characteristics of both flexibility and stiffness and, in general, might be classified as semi-rigid. Low-density polyethylene has been found particularly effective, but other thermoplastic materials having similar properties may be used. The attachment ring has an outwardly-extending and generally planar flange portion 27 and an annular inner collar portion 28 which extends axially away from flange portion along the inner margin thereof. As shown clearly in FIGS. 2 and 3, the collar portion has an opening 29 concentric with the stoma-receiving opening 20 of the faceplate. The outer surface 28a of the collar portion is generally cylindrical. At its free end 28b, the collar portion is smoothly rounded as shown most clearly in FIG. 3.

Pouch component 11 typically has a pair of side walls 30 and 31 joined together at their outer peripheries by a marginal heat seal 32. Each of the walls is composed of at least a primary layer 30a, 31a and a protective interior layer 30b, 31b. In each case, the primary layer 30a, 31a is formed of a water-soluble material which is flexible and relatively tough and strong in a dry state. As used herein, the term "water-soluble" also includes materials that are water-dispersible. Thus, the primary layer might be formed of tissue paper or similar cellulosic materials that provide substantial strength when dry but disintegrate quickly when exposed to water. However, in general, it is believed preferable to form the primary layers 30a, 31a of plastic films composed of water-soluble polymers such as polyvinyl alcohol, methyl hydroxypropyl cellulose, polyethylene oxide, or carboxymethyl cellulose. If desired, an additional layer of water-dispersible tissue paper may be secured to the outside of the pouch along primary layers 30a and 31a to promote patient comfort and enhance the rate of dissolution of the primary layers when the pouch is discarded into a flush toilet, since the highly absorbent and hydrophillic nature of such tissue paper is believed useful in ensuring that the outer surfaces of the primary layers are exposed to water. It is believed apparent that the structural integrity of the pouch 11 when the appliance is being worn is attributable to the primary layers 30a and 31a. In contrast the interior layers 30b, 31b are relatively thin and weak, serving essentially as protective coatings to prevent direct exposure of the primary layers to the contents of the pouch. Because of their composition and/or thinness,. the inner layers 30b, 31b lack sufficient strength to maintain the integrity of the pouch when the primary layers 30a, 31a have been dissolved or dispersed. Hence, the walls of the pouch, when exposed to the turbulence of water in a flushed toilet, readily dissolve and disintegrate. The interior layers or coatings may be formed of polyvinylene chloride, atactic propylene nitrocellulose, or any other suitable water-insoluble material known in the art.

As shown most clearly in FIG. 2, wall 31 has an opening 34 therethrough which defines a side opening or stoma-receiving opening for the pouch. An external mounting ring 35 circumscribes the pouch opening and is coated along its outer surface (i.e., the surface facing away from the pouch) with an annular layer 36 of pressure-sensitive adhesive. All of the layers are secured together by an annular heat seal 37, and a suitable release sheet 38 (shown in phantom) may cover the adhesive layer 36 prior to use of the product.

Mounting ring 35 is particularly useful in facilitating attachment and separation of components 11 and 12. For that purpose, the mounting ring may be provided with one or more peripheral extensions or tabs 35a which project radially outwardly beyond the remaining periphery of the mounting ring (FIG. 1). As shown in the drawings, the radial extent of tab 35a is substantially greater than the radius of the faceplate attachment ring 26 so that a user may readily grip the tab as the pouch is being manipulated to couple or uncouple the components 11, 12.

It will be noted that the surface of the attachment ring's flange portion 27 that faces pouch 11 is both smooth and planar to provide an effective surface for sealing contact with adhesive layer 36 of the pouch. The mounting ring 35 of the pouch is preferably formed of the same water-soluble polymeric material as layer 31a of wall 31 to which mounting ring 35 is heat sealed. It will be observed that when the components 11, 12 are separated, the edges 31c, 31d, and 35b which define the side opening 34 of the pouch are all exposed and, therefore, if edges 31d and 35b were exposed to an aqueous fluid, dissolution of the polymeric material or materials would commence along those edges. Such edges are not protected from exposure by any insoluble element of the pouch component and, hence, the pouch has no protective ring that would remain in the bowl or sewer system after the remainder of the pouch has dissolved and/or dispersed. Pouch 11 may therefore be accurately described as a "flushable" component which is fully dissolvable and/or dispersible following use. However, during use, when the pouch and faceplate components are joined together, edges 31d and 35b of the dissolvable layers are shielded from direct contact with fluid passing through the opening 29 of the attachment ring by means of the annular collar 28. The diameter of the collar's smooth, cylindrical, outside surface 28a is the same or only slightly less than the diameter of pouch wall opening 34, and the axial dimension of collar 28 exceeds the total thickness of wall 31 (including the thickness of mounting ring 35 and adhesive layer 36).

In addition to performing a shielding function, collar 28 serves as a locating collar to ensure proper alignment of the parts as they are being coupled together. The rounded end surface 28b of the collar is useful in re-orienting the parts should slight misalignment occur at the commencement of a coupling operation.

It might be observed that during use of the appliance, as pouch 11 collects discharge, it is conceivable that some of the fluid contents of the pouch might travel in a reverse direction and enter any slight annular spacing that might exist between the outer surface 28a of the collar and the inner edges 31c, 31d and 35b of the pouch opening. Such contact might occur, it at all, only after the pouch has been worn for a period of time and, since such a flushable pouch would ordinarily be replaced at frequently intervals, it is expected that the pouch would be discarded and replaced before any significant dissolution along the edges of the water-soluble layers could occur.

While in the foregoing an embodiment of the invention has been disclosed in considerable detail for purposes of illustration, it will be understood by those skilled in the art that many of these details may be varied without departing from the spirit and scope of the invention.

We claim:

1. A two-piece ostomy appliance comprising a faceplate component and a flushable pouch component;

said faceplate component comprising a thin, flexible, adhesive-coated patch having a stoma-receiving opening and a relatively stiff but flexible attachment ring of water-insoluble material secured to said patch about said opening;

said attachment ring having a thin outer flange portion and an inner annular collar portion extending axially away from both said flange portion and said patch and having an opening concentric with said stoma-receiving opening of said patch;

said pouch component having a pair of side walls joined together along their outer margins and each comprising a primary layer of strong but water-soluble material capable of quickly dissolving in the water of a toiletbowl in which the pouch is discardable and a protective inner layer of relatively weak but water-insoluble material incapable of maintaining the structural integrity of said pouch component when said primary layer is dissolved;

one of aid walls having a side opening therethrough along which edges of said primary and protective layers of said one wall are exposed;

said collar portion having an outer surface with an axial length greater tan the thickness of said one wall and with a diameter the same or slightly less than that of said side opening, whereby, said collar portion shields said exposed edges of said layers about said side opening of said pouch component from contact with fluids passing therethrough;

and means for releasably securing said pouch component to said attachment ring.

2. The appliance of claim 1 in which said means for releasably securing said pouch to said attachment ring comprises a layer of pressure-sensitive adhesive between said attachment ring and said pouch component.

3. The appliance of claim 2 in which said layer of pressure-sensitive adhesive is provided by said pouch component;

said outer flange portion of said attachment ring providing a smooth, continuous annular surface for sealingly engaging said layer of pressure-sensitive adhesive.

4. The appliance of claim 3 in which said smooth, annular surface of said flange portion is planar.

5. The appliance of claim 3 in which a flexible mounting ring is externally affixed to said one wall of said pouch component about said side opening;

said adhesive layer being located on a surface of said mounting ring facing said flange portion when said components are joined together.

6. The appliance of claim 5 in which said mounting ring is formed of water-soluble polymeric material.

7. The appliance of claims 5 or 6 in which said mounting ring has at least a portion thereof with a radius greater than the radius of said flange portion of said attachment ring to provide means for gripping the periphery of said mounting ring during coupling and uncoupling of said mounting and attachment rings.

8. The appliance of claim 6 in which said mounting ring has an inner edge concentric with and of substantially the same diameter as said side opening of said one wall of said pouch component.

9. The appliance of claim 1 in which said outer surface of said collar portion is substantially cylindrical and said side opening of said pouch component is circular.

10. The appliance of claim 1 in which said collar portion has a smoothly rounded free end surface.

* * * * *